US00PP15403P2

(12) United States Plant Patent
van Rijn

(10) Patent No.: US PP15,403 P2
(45) Date of Patent: Dec. 7, 2004

(54) ***BOUGAINVILLEA* PLANT NAMED 'VERA LYNN'**

(50) Latin Name: *Bougainvillea spectabilis*
Varietal Denomination: Vera Lynn

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/805,603

(22) Filed: Mar. 20, 2004

(51) Int. Cl.[7] ..... A01H 5/00
(52) U.S. Cl. ..... Plt./256
(58) Field of Search ..... Plt./256

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Bougainvillea* plant named 'Vera Lynn', characterized by its upright, outwardly spreading and compact growth habit; thornless stems; roughly spherical inflorescences with numerous flowers; and pink-colored flower bracts.

1 Drawing Sheet

Botanical classification/cultivar designation: *Bougainvillea spectabilis* cultivar Vera Lynn.

BACKGROUND OF THE INVENTION

The present Invention relates to a new and distinct cultivar of *Bougainvillea* plant, botanically known as *Bougainvillea spectrabilis,* and hereinafter referred to by the name 'Vera Lynn'.

The new *Bougainvillea* is a naturally-occurring whole plant mutation of the *Bougainvillea spectabilis* cultivar Vera Deep Purple, disclosed in U.S. Plant Pat. No. 10,950. The new *Bougainvillea* was discovered and selected by the Inventor as a single flowering plant from within a population of plants of the cultivar Vera Deep Purple in a controlled environment in Schipluiden, The Netherlands in July, 2000. The selection of this plant was based on its attractive flower color.

Asexual reproduction of the new cultivar by cuttings at Schipluiden, The Netherlands since Fall, 2000, has shown that the unique features of this new *Bougainvillea* are stable and reproduced true to type in successive generations.

SUMMARY OF THE INVENTION

Plants of the cultivar Vera Lynn have not been observed under all possible environmental conditions. The phenotype may vary somewhat with variations in environment such as temperature and/or light intensity without, however, any variance in genotype.

The following traits have been repeatedly observed and are determined to be the unique characteristics of 'Vera Lynn'. These characteristics in combination distinguish 'Vera Lynn' as a new and distinct cultivar:

1. Upright, outwardly spreading and compact growth habit.
2. Thornless stems.
3. Roughly spherical inflorescences with numerous flowers.
4. Pink-colored flower bracts.

Plants of the new *Bougainvillea* differ from plants of the parent cultivar, Vera Deep Purple, primarily in flower bract coloration as plants of the cultivar Vera Deep Purple have purple-colored flower bracts.

Plants of the new *Bougainvillea* differ from plants of the cultivar Vera Pink, disclosed in U.S. Plant patent application Ser. No. 10/805,578 filed concurrently, primarily in flower bract coloration as plants of the cultivar Vera Pink have lighter pink-colored flower bracts than plants of the new *Bougainvillea.*

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which accurately describe the colors of the new *Bougainvillea.*

The photograph comprises a side perspective view of a typical plant of 'Vera Deep Purple', left, and 'Vera Lynn', right.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Schipluiden, The Netherlands in a glass-covered greenhouse in containers during the spring. During the production of the plants, day temperatures were about 26° C. and night temperatures were about 25° C. Plants used for the aforementioned photograph and following description were about one year old.

Botanical classification:
*Bougainvillea spectabilis* cultivar Vera Lynn.

Parentage: Naturally-occurring whole plant mutation of the *Bougainvillea spectabilis* cultivar Vera Deep Purple, disclosed in U.S. Plant Pat. No. 10,950.

Propagation:
*Type.*—By cuttings.
*Time to initiate roots.*—About 8 to 10 days at 25° C.

*Time to develop roots.*—About 10 to 14 days at 25° C.

*Root description.*—Fibrous and freely branching.

Plant description:

*Form.*—Upright, outwardly spreading and compact growth habit.

*Plant height, soil level to top of plant plane.*—About 23 cm.

*Plant width.*—About 19 cm.

*Lateral branch description.*—Quantity: About three per plant. Length: About 4.3 cm. Diameter: About 2.7 mm. Internode length: About 9 mm. Texture: Thornless; densely pubescent. Color: 144B.

*Foliage description.*—Arrangement: Alternate, simple. Length: About 6.8 cm. Width: About 4.7 mm. Shape: Ovate to broadly ovate. Apex: Apiculate. Base: Attenuate. Margin: Entire; undulate. Texture, upper and lower surfaces: Smooth, glabrous. Luster, upper and lower surfaces: Moderately glossy. Venation pattern: Pinnate. Color: Developing foliage, upper surface: 143A. Developing foliage, lower surface: 143C. Fully expanded foliage, upper surface: Between 137A and 139A. Fully expanded foliage, lower surface: 137B to 137C. Venation, upper surface: 144A. Venation, lower surface: 144B. Petiole length: About 1.6 cm. Petiole diameter: About 1.5 mm. Petiole color: 143A.

Flower description:

*Flower type and habit.*—Single flowers arranged in axillary compound cymes with showy and colorful bracts; cymes roughly spherical. Flowers face outward and upright. Flowers not persistent.

*Fragrance.*—None.

*Natural flowering season.*—Continuously flowering from spring throughout the summer in Schipluiden, The Netherlands.

*Quantity.*—Freely flowering with about 21 flowers per cyme.

*Flower longevity on the plant.*—About one week.

*Inflorescence height.*—About 9 cm.

*Inflorescence diameter.*—About 8.5 cm.

*Flower diameter.*—About 7 mm.

*Flower depth (height).*—About 2 mm.

*Flower buds.*—Length: About 7 mm. Diameter: About 2 mm. Shape: Oblanceolate; apex, rounded. Color: 146C to 146D; towards the apex, 39B.

*Petals.*—Quantity per flower: About five; fused tubular corolla. Length: About 2 cm. Width: About 3.5 mm. Shape: Narrowly flabellate. Apex: Emarginate. Margin: Entire. Texture, upper and lower surfaces: Smooth; glabrous. Color: When opening and fully opened, upper surface: 155D. When opening and fully opened, lower surface: 155D.

*Sepals.*—Quantity per flower: About five; fused tubular corona. Length: About 1.9 cm. Diameter: About 1.5 mm. Shape: Roughly lanceolate. Apex: Acute. Margin: Entire. Color: When opening and fully opened, upper surface: 146C to 146D. When opening and fully opened, lower surface: 146C to 146D; towards the apex, 179B.

*Pedicels.*—Length: About 2.1 cm. Diameter: About 1 mm. Angle: Erect to about 30° from vertical. Strength: Moderate. Color: 144A.

*Flower bracts.*—Quantity per flower: One; showy and colorful. Length: About 4.2 cm. Width: About 3.6 mm. Shape: Broadly ovate. Apex: Obtuse to abruptly acute. Base: Cordate. Margin: Entire. Texture, upper and lower surfaces: Smooth, glabrous. Color: When opening, upper and lower surfaces: 64D. Fully opened, upper and lower surfaces: 64C to 64D; venation, 144A.

*Reproductive organs.*—Androecium: Stamens per flower: About eight. Stamen length: About 1.2 cm. Anther shape: Oval. Anther length: About 0.5 mm. Anther color: 13A. Pollen amount: Scarce. Pollen color: 13B to 13C. Gynoecium: Quantity of pistils per flower: One. Pistil length: About 4.5 mm. Stigma shape: Linear. Stigma color: N155A. Style length: About 1.5 mm. Style color: 144B. Ovary color: 144B.

*Seeds/fruits.*—Seed and fruit development has not been observed.

Disease/pest resistance: Under commercial production conditions, plants of the new *Bougainvillea* have not been noted to be resistant to pathogens or pests common to *Bougainvillea*.

Temperature tolerance: Plants of the new *Bougainvillea* have been observed to tolerate temperatures from 3 to 40° C. in Schipluiden, The Netherlands.

It is claimed:

1. A new and distinct cultivar of *Bougainvillea* plant named 'Vera Lynn', as illustrated and described.

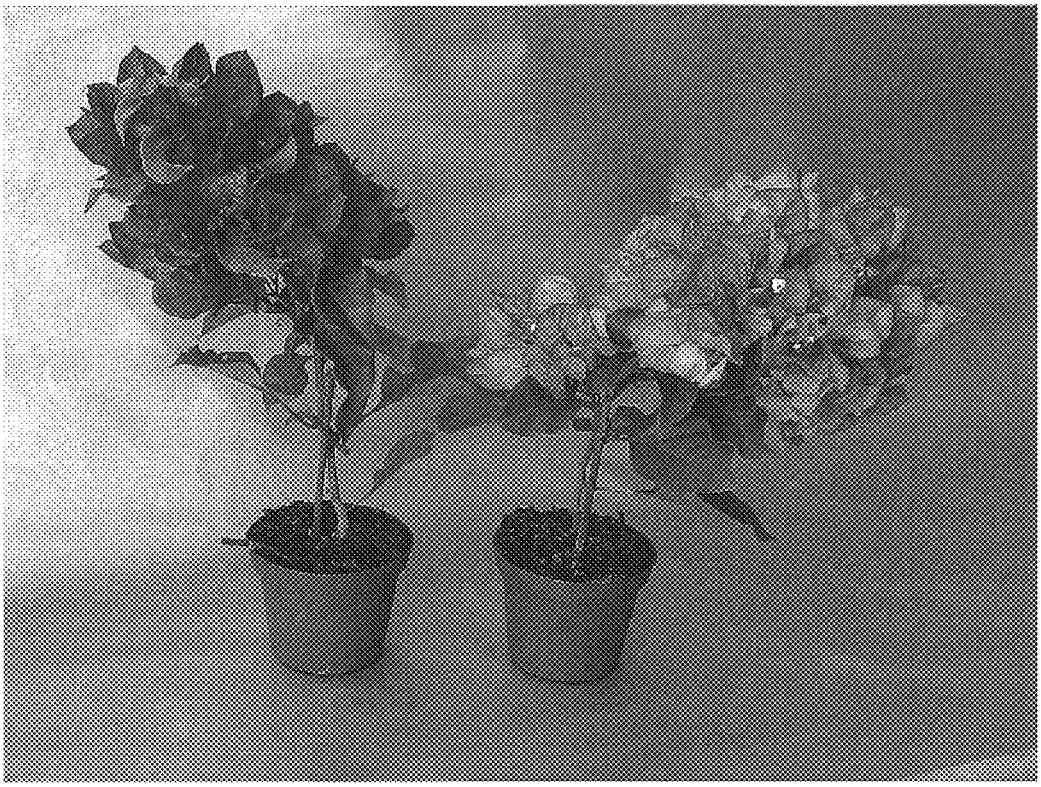

* * * * *